United States Patent
Yoshpe et al.

(10) Patent No.: US 10,245,241 B2
(45) Date of Patent: Apr. 2, 2019

(54) NASAL IRRIGATION

(71) Applicants: Nina S Yoshpe, Huntington Beach, CA (US); Ayal Willner, Newport Beach, CA (US); Rafael Akyuz, Torrance, CA (US)

(72) Inventors: Nina S Yoshpe, Huntington Beach, CA (US); Ayal Willner, Newport Beach, CA (US); Rafael Akyuz, Torrance, CA (US)

( * ) Notice: Subject to any disclaimer, the term of this patent is extended or adjusted under 35 U.S.C. 154(b) by 85 days.

(21) Appl. No.: 15/170,706

(22) Filed: Jun. 1, 2016

(65) Prior Publication Data

US 2017/0348260 A1  Dec. 7, 2017

(51) Int. Cl.

| A61K 9/00 | (2006.01) |
|---|---|
| A61K 31/19 | (2006.01) |
| A61K 47/02 | (2006.01) |
| A61K 47/12 | (2006.01) |
| A61K 47/26 | (2006.01) |
| A61K 31/047 | (2006.01) |

(52) U.S. Cl.
CPC ............ A61K 31/19 (2013.01); A61K 9/0043 (2013.01); A61K 31/047 (2013.01); A61K 47/02 (2013.01); A61K 47/12 (2013.01); A61K 47/26 (2013.01)

(58) Field of Classification Search
CPC ...... A61K 31/047; A61K 31/19; A61K 47/02; A61K 47/1226; A61K 9/0043
See application file for complete search history.

(56) References Cited

U.S. PATENT DOCUMENTS 7,192,919 B2 * 3/2007 Tzannis ................ A61K 38/28
514/5.9

OTHER PUBLICATIONS

SinuAir (https://www.sinupulse.com/index.php?p=Powder, 2015).*
Chen and Davidson (Geriatric Otolaryngology, 2006, Ed. Calhoun et al. p. 232, para 2).*
Grossan (http://www.grossaninstitute.com/three-steps-clear-infection-chronic-sinusitis-cystic-fibrosis/,2014).*
Weissman (The Laryngoscope, 2011).*
Himedia (http://himedialabs.com/TD/M525.pdf, 2015) (Year: 2015).*
Powders (Quizlet, 2014, https://quizlet.com/64695876/powders-flash-cards/DEC 9 2014). (Year: 2014).*
Tsu-Hui Low et al., "A double-blind randomized controlled trial of normal saline, lactated Ringer's, and hypertonic saline nasal irrigation solution after endoscopic sinus surgery", published by http://connection.ebscohost.com/c/articles/95934632/double-blind-randomized-controlled-trial-normal-saline-lactated-ringers-hypertonic-saline-nasal-irrigation-solution-after-endoscopic-sinus-surgery#.VCL8p8OwQCU.gmail on May 2014.
Unal M. et al., "Ringer-Lactate solution versus isotonic saline solution on mucociliary function after nasal septal surgery", published by http://www.ncbi.nlm.nih.gov/m/pubmed/11667990/ in Oct. 2001.

* cited by examiner

*Primary Examiner* — Umamaheswari Ramachandran
(74) *Attorney, Agent, or Firm* — LeonardPatel PC

(57) ABSTRACT

A nasal irrigation solution (or composition) for pre- and post-operation sinus surgery and for use as a daily nasal cleanser. The composition, which may be in a powder form, may include lactated ringers with xylitol. This composition may be mixed with sterile water prior to nasal irrigation.

7 Claims, 1 Drawing Sheet

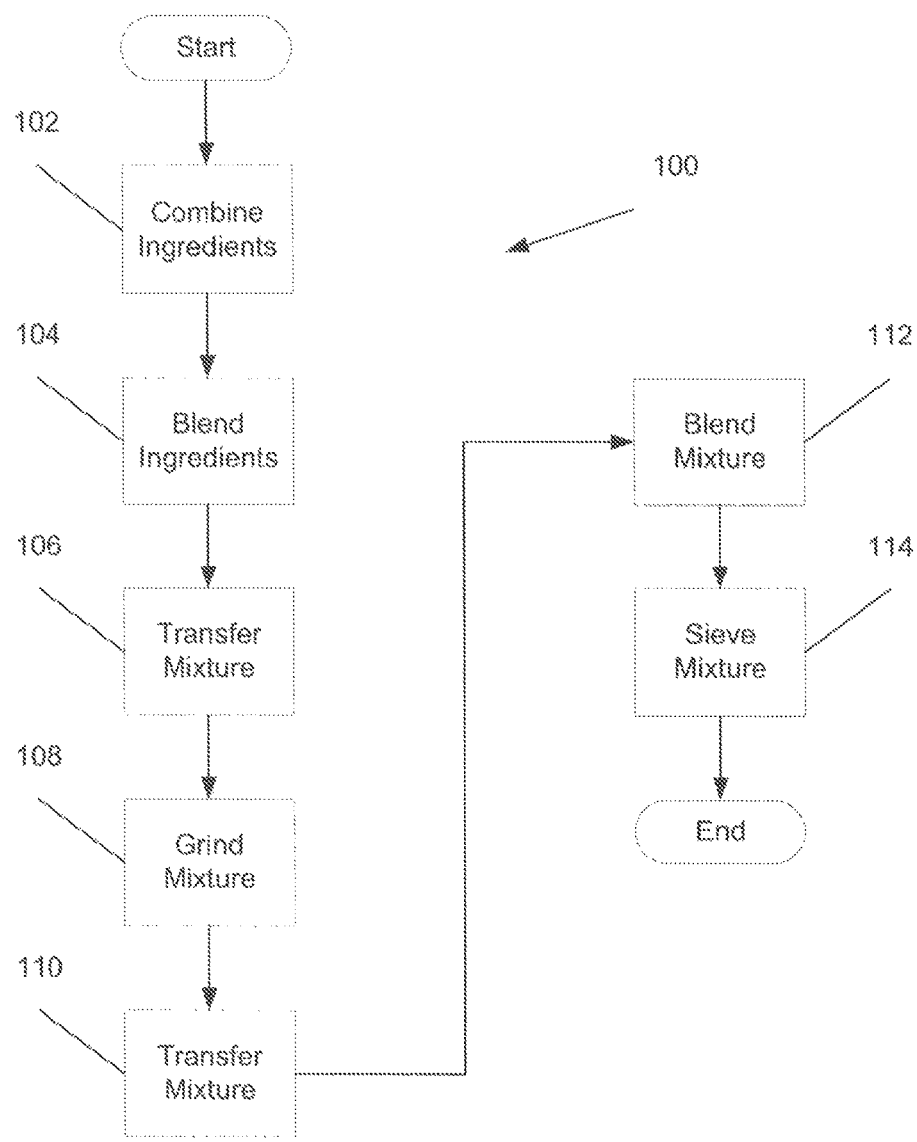

NASAL IRRIGATION

FIELD

The present invention generally relates to nasal irrigation, and more particularly, to the use of lactated ringers with xylitol in a powder form for nasal irrigation.

BACKGROUND

Nasal secretions, which contribute to a stuffy or congested nose, occur when the tissues lining the nose become swollen. This may lead to inflammation and biofilm formation which is difficult to remove without irrigation.

The combination of nasal saline with water has been used since the $15^{th}$ century for nasal irrigation. Nasal irrigation is the mechanical flushing of the nasal mucosa, which aids in removing the abnormal or excessive buildup of nasal secretions. Nasal irrigation is widely used and accepted in the medical community as a nasal cleansing procedure and after sinus surgery of the nose and sinus cavities.

During a sinus infection, there is accumulation of mucous, which contributes to loss of normal ciliary function of the respiratory mucosa. The virus and/or bacteria may also damage and inhibit the nasal cilia. The purpose of nasal irrigation is to remove the excess accumulation of mucous, which occurs during a sinus infection and/or after sinus surgery. Nasal irrigation after sinus surgery has been shown to be effective with both isotonic and hypertonic saline.

However, saline has been known inhibit normal nasal ciliary functions. In some cases, saline can also precipitate on the nasal mucousa. Thus, a more effective nasal irrigation solution may be beneficial.

SUMMARY

Certain embodiments of the present invention may provide solutions to the problems and needs in the art that have not yet been fully identified, appreciated, or solved by conventional nasal irrigation solutions. For example, some embodiments generally pertain to a novel approach of combining lactated ringers with xylitol and reducing the combination of lactated ringers with xylitol in a powder form to be used with sterile water for nasal irrigation. This may provide a unique combination of both cilia preserving and antibacterial components not otherwise realized in current nasal saline solutions. The powder may be compounded and packaged in an anhydrous environment, for example, to be used by both children and adults. The powder may be used for pre- and post-operation sinus surgeries, as well as for a daily nasal cleanser.

In an embodiment, a process for reducing lactated ringers in a powder form for nasal irrigation may include blending sodium chloride, sodium lactate powder, potassium chloride, and calcium chloride in a blender to create a uniform mixture. The process may further include grinding the uniform mixture comprising sodium chloride, sodium lactate, powder, potassium chloride, and calcium chloride. The process may also include blending the grinded uniform mixture comprising sodium chloride, sodium lactate powder, potassium chloride, and calcium chloride, and include sieving the blended mixture to reduce the blended mixture to the powder form for use in nasal irrigation.

In another embodiment, a process for reducing lactated ringers with xylitol in a powder form for nasal irrigation may include blending sodium chloride, sodium lactate powder, potassium chloride, calcium chloride, and xylitol in a blender to create a uniform mixture. The process may also include grinding the uniform mixture comprising sodium chloride, sodium lactate, powder, potassium chloride, calcium chloride, and xylitol. The process may further include blending the grinded uniform mixture comprising sodium chloride, sodium lactate powder, potassium chloride, calcium chloride, and xylitol, and include sieving the blended mixture to reduce the blended mixture to the powder form for use in nasal irrigation.

In yet another embodiment, a process for reducing a nasal irrigation composition to powder form may include mixing one or more active ingredients in a blender. The one or more active ingredients may include sodium chloride, sodium lactate powder, potassium chloride, calcium chloride, and xylitol. The process may include blending the one or more active ingredients until a uniform mixture is reached. The process may also include grinding the uniform mixture of the one or more active ingredients for a predefined period of time to achieve and lower a granular size and to decrease the size of the uniform mixture. The process may further include blending the grinded uniform mixture of the one or more active ingredients until a uniformity is achieved between the one or more of the active ingredients, and include sieving the blended mixture of the one or more active ingredients to reduce the blended mixture to the powder form.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 1 illustrates a compounding process for reducing lactated ringers with xylitol to powder form, according to an embodiment of the present invention.

DETAILED DESCRIPTION OF THE EMBODIMENTS

Some embodiments of the present invention generally pertain to a nasal irrigation solution (or composition) for pre- and post-operation sinus surgery and for use as a daily nasal cleanser. In some embodiments, the composition, which may be in a powder form, may include lactated ringers, and in some further embodiments, the lactated ringers may be combined with xylitol. This composition may be mixed with sterile water prior to nasal irrigation.

In some embodiments, the composition may include, but is not limited to, the following active ingredients reduced to powder form: sodium chloride, sodium lactate, potassium chloride, calcium chloride, and/or erthritol/xylitol.

The composition in Table 1 below generally shows the sources of individual components in some embodiments.

TABLE 1

Percentage Formula

| | | % By Weight |
|---|---|---|
| Sodium Chloride U.S.P. | (Spectrum) | 60.50 |
| Sodium Lactate Powder, Purasol Powder S100 | (Lotion Crafter) | 32.30 |
| Potassium Chloride U.S.P | (Spectrum) | 3.12 |
| Calcium Chloride, Dihydrate U.S.P. | (Spectrum) | 2.08 |
| Erythritol/Xylitol | (Lite Sweet/Xlear) | 2.00 |
| Total | | 100.00 |

In some embodiments, the composition may be prepared as shown in Table 2 below.

TABLE 2

Compounding Formula
Batch Size: 1,000 lbs.

| | | By Weight (lbs.) |
|---|---|---|
| Part A | Sodium Chloride U.S.P. | 605.00 |
| | Sodium Lactate Powder, Purasol Powder S100 | 323.0 |
| | Potassium Chloride U.S.P. | 31.20 |
| | Calcium Chloride, Dihydrate U.S.P. | 20.80 |
| | Erythritol/Xylitol | 20.00 |
| Total | | 1,000.00 |

FIG. 1 illustrates a compounding process 100 for reducing the lactated ringers with xylitol to powder form, according to an embodiment of the present invention. In some embodiments, the active ingredients discussed above may be combined in a Patterson Kelley (PK) blender at 102. At 104, the ingredients are blended until a uniform mixture is reached. The uniform mixture in some embodiments means that every part of the mixture has the same properties. Put simply, the ingredients (or formula) in some embodiments may have a uniform physical appearance and a uniform chemical characteristic to acquire the expected results. At 106, the uniform mixture is transferred into a grinder, and at 108, the uniform mixture is grinded. It should be appreciated that the purpose of grinding the uniform mixture is to achieve and lower the granular size and to bring the mixture to a small and uniform size. The time period for grinding may depend on achieving uniformity of each ingredient. In some embodiments, for example, the uniform mixture may be grinded for approximately 10 minutes. At 110, the grinded mixture is transferred to a PK blender, and at 112, the grinded mixture is blended until a uniform mixture is achieved. At 114, the uniform mixture is sieved through a mesh screen, resulting in the compositions final powder form. In some embodiments the uniform mixture is sieved through a 100 mesh screen, for example. This not only allows for uniformity, but also allows for an exact amount for each ingredient in the powder form to be filled within a smaller package.

It should be appreciated that the powder may be a hygroscopic mixture in some embodiments. Due to its hygroscopic mature in these embodiments, the powder should be protected from humidity until placed into a packet. For example, the powder should be placed in a sealed packaging to protect the product from moisture and air.

Once the product is placed within a sealed packaging, the packaging may be opened at a later time for use. For example, powder may be removed from the sealed packaging and be placed in a 240 ml bottle containing distilled water.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics that may be combined in any suitable manner in one or more embodiments.

It should be noted that reference throughout this specification to features, advantages, or similar language does not imply that all of the features and advantages may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A process for producing and protecting a hygroscopic mixture powder comprising xylitol for use in nasal irrigation, the process comprising:

blending chemical compounds that formulate lactated ringers in a blender to create a uniform mixture, wherein the chemical compounds comprise sodium chloride, sodium lactate powder, potassium chloride, calcium chloride, and xylitol;

grinding the uniform mixture comprising sodium chloride, sodium lactate, powder, potassium chloride, calcium chloride, and xylitol;

blending the grinded uniform mixture comprising sodium chloride, sodium lactate powder, potassium chloride, calcium chloride, and xylitol;

sieving the blended mixture to reduce the blended mixture into the hygroscopic mixture of the lactated ringers with xylitol, for use in nasal irrigation; and protecting the hygroscopic mixture from moisture and air by inserting the hygroscopic mixture in a sealed package to protect the hygroscopic mixture from moisture and air, wherein the blending of the chemical compounds comprise 60.50% wt. of sodium chloride, 32.30% wt. of sodium lactate powder, 3.12% wt. of potassium chloride, 2.08% wt. of calcium chloride, and 2.00% wt. of xylitol.

2. The process of claim 1, wherein the grinding of the uniform mixture comprises grinding the uniform mixture until uniformity between sodium chloride, sodium lactate, powder, potassium chloride, calcium chloride, and xylitol is achieved.

3. The process of claim 1, wherein the sieving of the blended mixture comprises sieving through a mesh screen to achieve uniformity between sodium chloride, sodium lactate powder, potassium chloride, calcium chloride, and xylitol in the powder form.

4. A process for producing and protecting hygroscopic nasal irrigation powder of lactated ringers, comprising:

mixing one or more active ingredients in a blender, wherein the one or more active ingredients comprises lactated ringers or lactated ringers and xylitol;

blending the one or more active ingredients until a uniform mixture is reached;

grinding the uniform mixture of the one or more active ingredients for a predefined period of time to achieve and lower a granular size and to decrease the size of the uniform mixture;

blending the grinded uniform mixture of the one or more active ingredients until a uniformity is achieved between the one or more of the active ingredients;

sieving the blended mixture of the one or more active ingredients to reduce the blended mixture into the hygroscopic nasal irrigation powder; and protecting the powder form from moisture and air by inserting the hygroscopic nasal irrigation powder in a sealed package that protects the hygroscopic nasal irrigation from moisture and humidity, wherein the blending of the chemical compounds comprise 60.50% wt. of sodium chloride, 32.30% wt. of sodium lactate powder, 3.12% wt. of potassium chloride, 2.08% wt. of calcium chloride, and 2.00% wt. of xylitol.

5. The process of claim 4, wherein the grinding of the uniform mixtures depends on the uniformity of the one or more active ingredients.

6. The process of claim 4, wherein the blending of the chemical compounds comprise 605.00 lbs. of sodium chloride, 323.0 lbs. of sodium lactate powder, 31.20 lbs. of potassium chloride, and 20.80 lbs. of calcium chloride.

7. The process of claim 1, wherein the blending of the chemical compounds comprise 605.00 lbs. of sodium chloride, 323.0 lbs. of sodium lactate powder, 31.20 lbs. of potassium chloride, and 20.80 lbs. of calcium chloride, and 20.00 lbs. of xylitol.

* * * * *